US009304334B2

(12) United States Patent
Progler

(10) Patent No.: US 9,304,334 B2
(45) Date of Patent: Apr. 5, 2016

(54) MICROFLUIDIC THERMOPTIC ENERGY PROCESSOR

(71) Applicant: PHOTRONICS, INC., Brookfield, CT (US)

(72) Inventor: Christopher J. Progler, Plano, TX (US)

(73) Assignee: PHOTRONICS, INC., Brookfield, CT (US)

( * ) Notice: Subject to any disclaimer, the term of this patent is extended or adjusted under 35 U.S.C. 154(b) by 0 days.

(21) Appl. No.: 14/160,142

(22) Filed: Jan. 21, 2014

(65) Prior Publication Data

US 2014/0204450 A1     Jul. 24, 2014

Related U.S. Application Data

(60) Provisional application No. 61/754,746, filed on Jan. 21, 2013.

(51) Int. Cl.

| | |
|---|---|
| *G01N 21/00* | (2006.01) |
| *G01N 27/00* | (2006.01) |
| *G02F 1/01* | (2006.01) |
| *F28D 20/00* | (2006.01) |
| *G01N 27/447* | (2006.01) |
| *G06F 3/041* | (2006.01) |
| *H01L 35/30* | (2006.01) |
| *F24J 2/20* | (2006.01) |
| *F24J 2/40* | (2006.01) |
| *F24J 2/48* | (2006.01) |
| *E06B 3/67* | (2006.01) |
| *G02F 1/1333* | (2006.01) |

(52) U.S. Cl.
CPC ............... *G02F 1/0147* (2013.01); *F24J 2/202* (2013.01); *F24J 2/407* (2013.01); *F24J 2/482* (2013.01); *F28D 20/0034* (2013.01); *G01N 27/44704* (2013.01); *G01N 27/44782* (2013.01); *G06F 3/041* (2013.01); *H01L 35/30* (2013.01); *E06B 3/6722* (2013.01); *G02F 1/13338* (2013.01); *G02F 2201/30* (2013.01); *G02F 2203/62* (2013.01); *Y02E 60/142* (2013.01); *Y10T 137/2213* (2015.04); *Y10T 137/2224* (2015.04)

(58) Field of Classification Search
CPC . G01N 21/05; G01N 21/75; G01N 27/44704; G01N 27/44782
USPC ................... 359/642; 204/602, 603; 250/573; 422/68.1, 82.05
See application file for complete search history.

(56) References Cited

U.S. PATENT DOCUMENTS

| | | | | |
|---|---|---|---|---|
| 6,033,546 | A   * | 3/2000 | Ramsey | ......................... 204/603 |
| 2004/0005582 | A1* | 1/2004 | Shipwash | ......................... 435/6 |
| 2004/0101444 | A1* | 5/2004 | Sommers et al. | ............. 422/100 |

\* cited by examiner

*Primary Examiner* — William Choi
(74) *Attorney, Agent, or Firm* — Amster, Rothstein & Ebenstein LLP

(57) ABSTRACT

A microfluidic panel including at least one substrate, one or more channels formed in the substrate, and fluid disposed within the one or more channels. The fluid is selected to store thermal energy and the microfluidic panel is adapted to convert the thermal energy into useable energy or condition the energy to adjust optical wavelength passband of the panel.

18 Claims, 4 Drawing Sheets

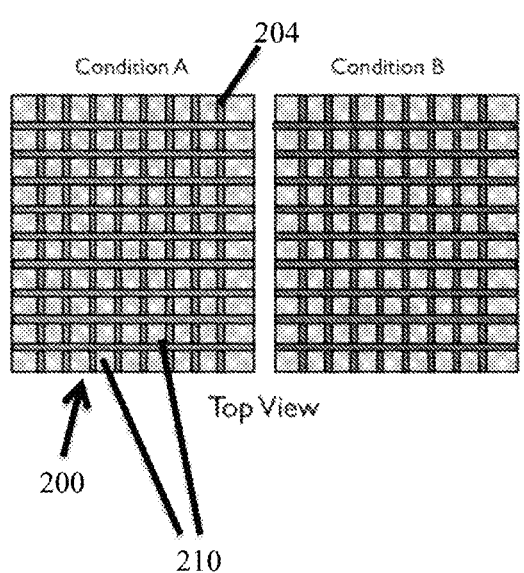
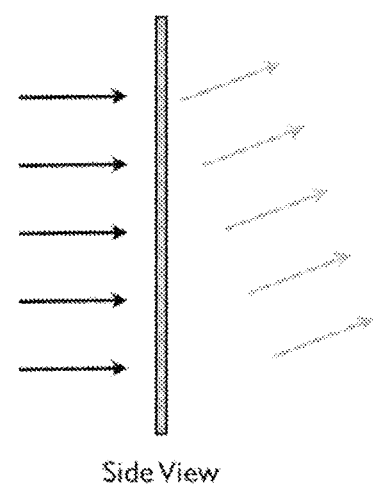
FIG. 2A  FIG. 2B  FIG. 2C

MICROFLUIDIC THERMOPTIC ENERGY PROCESSOR

FIELD OF THE INVENTION

The present disclosure relates to microfluidic devices, and in particular to microfluidic devices used for conversion and/or conditioning of energy.

SUMMARY OF THE INVENTION

According to an exemplary embodiment of the present invention, a microfluidic panel comprises at least one substrate, one or more channels formed in the substrate, and fluid disposed within the one or more channels.

In at least one embodiment, the fluid is selected to store thermal energy and the microfluidic panel is adapted to convert the thermal energy into useable energy.

In at least one embodiment, the fluid is selected to store thermal energy and the microfluidic panel is adapted to condition the energy to adjust optical wavelength passband of the panel.

In at least one embodiment, the microfluidic panel further comprises a cover disposed over the substrate.

In at least one embodiment, the at least one substrate is made of glass.

In at least one embodiment, the glass comprises one or more types of glass selected from the group consisting of: fused silica glass, borosilicate glass and photo-structurable glass.

In at least one embodiment, the one or more channels comprise a plurality of channels that form a grid.

In at least one embodiment, the one or more channels comprise a channel that follows a serpentine path.

In at least one embodiment, the microfluidic panel further comprises at least one thermoelectric generator.

In at least one embodiment, the microfluidic panel further comprises at least one pump that causes the fluid to flow through the one or more channels.

In at least one embodiment, the at least one pump is a micro-electromechanical system (MEMS) pump.

In at least one embodiment, the at least one substrate comprises: a first glass layer; a first gas layer disposed over the first glass layer; a first acrylic layer disposed over the first gas layer; a second acrylic layer disposed over the first acrylic layer; a second gas layer disposed over the second acrylic layer; and a second glass layer disposed over the second gas layer.

In at least one embodiment, the one or more channels are formed in at least one of the first or second acrylic layers.

In at least one embodiment, the one or more channels are formed in a glass substrate disposed between the first and second acrylic layers.

In at least one embodiment, the microfluidic panel further comprises heat mirror disposed below the first acrylic layer.

In at least one embodiment, surfaces of the first and second acrylic layers closest to the one or more channels are coated with silicon carbide.

These and other features of this invention are described in, or are apparent from, the following detailed description of various exemplary embodiments of this invention.

BRIEF DESCRIPTION OF THE DRAWINGS

The features and advantages of the present invention will be more fully understood with reference to the following, detailed description of an illustrative embodiment of the present invention when taken in conjunction with the accompanying figures, wherein:

FIGS. 2A and 2B are planar views and FIG. 2C is a cross sectional view of a microfluidic panel according to another exemplary embodiment of the present invention;

DETAILED DESCRIPTION OF EMBODIMENTS OF THE PRESENT INVENTION

Figures 1A, 1B:
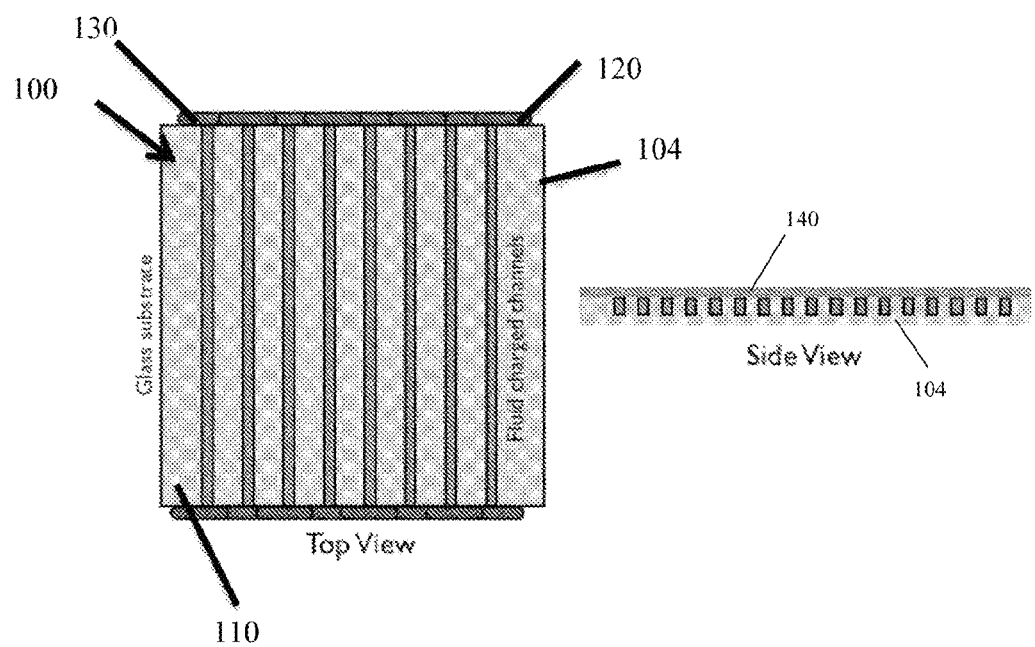
FIG. 1A is a planar view and FIG. 1B is a cross sectional view of a microfluidic panel according to an exemplary embodiment of the present invention.

Various exemplary embodiments of the present invention are directed to a microfluidic panel including a series or an array of microchannels formed in a substrate. The microchannels may be charged with a fluid. The panel may be used to capture impinging solar radiation or other thermal radiation through heating of fluid and subsequently converting the heated fluid into usable energy and/or conditioning energy impinging on the device to adjust the optical wavelength passband of the panel. In exemplary embodiments, the microfluidic panel may have applications in, for example, clean energy generation from solar radiation, smart or adaptive window glass technology, mobile battery charging, and automotive battery charging, to name a few.

A microfluidic panel according to an exemplary embodiment of the present invention may be made of large form factor glass panels with dense sub-visual resolution patterns. For example, the microfluidic panels may have dimensions from 100 square mm to over 2 meter square. The patterns formed in the panels may form channel arrays that hold static or flowing fluid. The dense patterns within the large form factor panels allow for the formation of channel arrays of extremely long length. For example, more than 60 miles of 2 micron wide channels can be formed in a 1 m square panel substrate. The microfluidic panel according to various exemplary embodiments of the present invention may provide unique value in a number of technological fields, such as, for example, life sciences, clean energy generation and environmental management, to name a few. For example, in the field of life sciences, the microfluidic panel may be integrated as part of a biological incubation system, aid in high compact, high volume wet process reduction, and provide a multi-function lab on chip platform. In the terms of clean energy, the microfluidic panel may function as a solar coupled thermal processor. In regards to environmental management, the microfluidic panel may provide optical pass band modulation and ambient environmental control.

In order to achieve some of the applications for the microfluidic panel according to exemplary embodiments of the present invention, fluid options with appropriate thermal and optical properties must be considered, including thermal and flow properties, optical activation and response time, and cost and durability factors. Thermal energy conversion options are also considered, and preferably such options exhibit viable efficiency, form factor and cost. Input and output options for ease of installation are another consideration, and may include factors such as pump mechanisms, sealing and bonding options, and packaging and integration. Other considerations include types of thin, transparent glass substrates suitable for precise patterning, large area patterning technology, and channel design.

In exemplary embodiments, channel design in particular is formulated to achieve goals such as, for example, maximum energy capture with minimum diffusion losses, depth, width and run length optimization and visually non-obtrusiveness with ability to impact bulk optical and thermal capture properties.

A microfluidic panel according to an exemplary embodiment of the present invention may include a substrate made of glass, such as, for example, fused silica or borosilicate glass, and/or other suitable materials, such as photo-structurable glass, or material comprising superior optical properties and biocompatibility. Channels may be formed within the substrate using lithography techniques, such as, for example, photolithography, X-ray lithography or electron beam lithography. The channels are preferably at sub-visual resolution, for example, at a width of less than 10 μm. The cross sectional shape of each channel is preferably chosen so as to minimize diffusion and drag. For example, although the cross sectional shape of the channels shown in FIGS. 1A and 1B are generally square with right angled corners, in other exemplary embodiments, the channels 10 may have more of a curved cross sectional shape.

A microfluidic panel according to an exemplary embodiment of the present invention may include channels arranged in a serpentine array or arranged in a cross-hatch pattern.

In an exemplary embodiment of the present invention, the microfluidic panel may be adapted to capture thermal radiation through heating of fluid within the channels and subsequently converting the heated fluid into usable energy. For example, the thermal radiation may be solar radiation. The fluid within the channels may be selected so as to capture thermal energy with high efficiency, and in at least one exemplary embodiment, may be carbon based nano-particles that store energy and exhibit low drag for efficient diffusion of the energy throughout the panel structure. Suitable nano-particles for thermal energy capture may include, for example, zinc sulphide, zinc oxide, cadmium selenide, indium phosphide, gold, silver, iron oxide, titanium dioxide, silicon, and silicon dioxide, to name a few. The selected fluid also preferably has relatively low viscosity for maintaining reasonable pressure within fluid wells.

The conversion of the heat held by the fluid within the microfluidic panel may be achieved using, for example, Rankine or Stirling engines. More specifically, such conversion may be achieved using a turbine, a condenser and pump, an evaporator or combinations of these components. The microfluidic panel may include one or more such conversion components. For example, according to an exemplary embodiment, the microfluidic panel may include an array of conversion components, where each conversion component may be controlled locally to achieve the desired energy output.

FIG. 1A is a planar view and FIG. 1B is a cross sectional view of a microfluidic panel, generally designated by reference number 100, according to an exemplary embodiment of the present invention. The transparent glass panel 100 may include a substrate 104 in which are formed a grid of channels 110. The channels 110 may carry fluids that store thermal energy generated from heat and/or radiation sources such as the infrared radiation of the sun. Thermal energy stored in heated fluids may be converted to electrical energy through use of thermoelectric generator 120 or other suitable heat conversion engine. Fluid may be pumped through channels 110 with low voltage micro-electromechanical system (MEMS) pump 130 in cascaded fashion. Thermoelectric generator (TEG) may be comprised of semiconductor materials that convert a temperature differential across the device and the resulting heat flow through the device into a voltage that may be used for the generation of useful electrical power. Suitable fluids for channel include water and water based solutions infused with nano-particles that contribute to improved heat retention and minimize drag of fluid within channels. Channels and surfaces may also be artificially structured with post, pillars and other physical constructs to expand or improve the coupling and retention of thermal energy within flowing fluid. A cover 140 may be bonded or otherwise attached to the substrate 104 so as to form upper surfaces of the channels 110.

FIGS. 2A and 2B are planar views and FIG. 2C is a cross sectional view of a microfluidic panel, generally designated by reference number 200, according to another exemplary embodiment of the present invention. In this embodiment, the transparent glass panel 200 is comprised of a grid of channels 210 carrying fluids in which said fluids and arrangement of channels 210 possess certain optical processing effects advantageous for the conditioning of incoming optical radiation. Index of refraction, color and flow of fluid are optimized to absorb, direct, diffract, refract and otherwise alter incoming optical radiation to induce environmental conditions between the two sides of the glass panel. Surface of channels and particularly areas where channels in various orientations intersect may be structured to induce certain effects such as the local storage of fluid in a well that may be reset or programmed with a flushing of well at a later time. As in the previous embodiment, a cover may be attached to the panel 200 to form upper surfaces of the channels 210.

By combining the thermal energy conversion effect as in the exemplary embodiment shown in FIGS. 1A and 1B with the optical processing effect as in the exemplary embodiment shown in FIGS. 2A, 2B and 2C, an integrated thermoptic device may be fabricated with the ability to generate useful electrical power while, at the same time, condition incoming optical radiation to enhance power generation and improve the ambient optical energy transferring through the panel for energy efficiency and aesthetic appeal.

Figure 3:
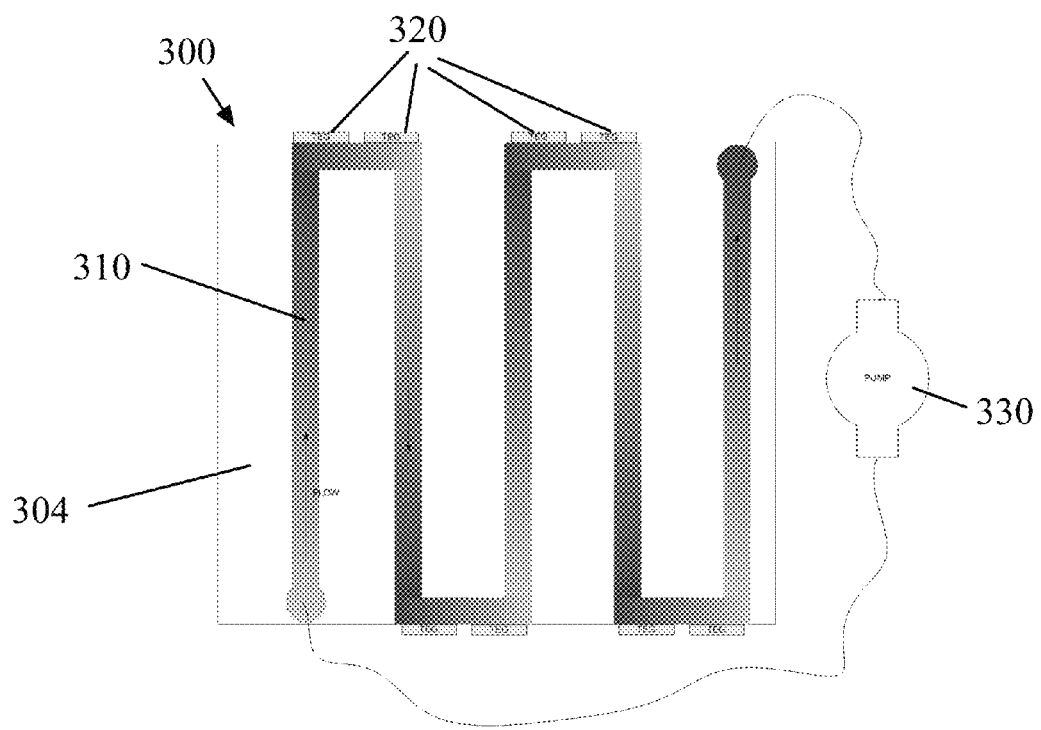
FIG. 3 is a planar view of a microfluidic panel according to another exemplary embodiment of the present invention.

FIG. 3 is a planar view of a microfluidic panel, generally designated by reference number 300, according to another exemplary embodiment of the present invention. The microfluidic panel 300 includes a substrate 304 in which is formed a channel 310. In the present embodiment, the channel 310 follows a serpentine path. The channel 310 may carry fluids that store thermal energy generated from heat and/or radiation sources such as the infrared radiation of the sun. Thermal energy stored in heated fluids may be converted to electrical energy through use of thermoelectric generators 320 or other suitable heat conversion engine. Fluid may be pumped through channel 310 with a pump 330, such as a low voltage micro-electromechanical system (MEMS) pump.

Figure 4:
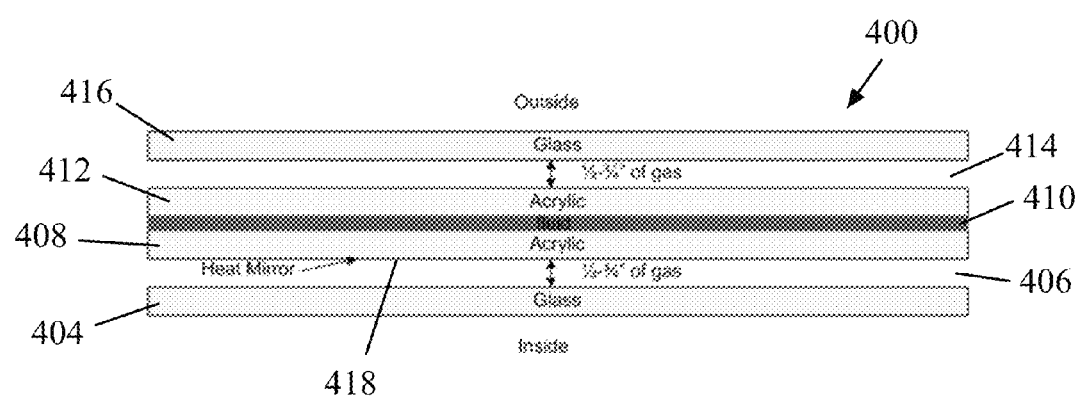
FIG. 4 is a cross-sectional view of a microfluidic panel according to another exemplary embodiment of the present invention.

According to an exemplary embodiment of the present invention, in order to enhance insulation of heat absorbed by the fluid within the channels, the microfluidic panel may be provided with one or more insulation layers. For example, as shown in FIG. 4, a microfluidic panel, generally designated by reference number 400, may include a first glass substrate 404, a first gas layer 406 formed over the first glass substrate 404, a first acrylic layer 408 formed over the first gas layer 406, a fluid channel layer 410 formed over the first acrylic layer 408, a second acrylic layer 412 formed over the fluid channel layer 410, a second gas layer 414 formed over the second acrylic layer 412 and a second glass substrate 416 formed over the second gas layer 414. In the embodiment shown in FIG. 4, thermal radiation is directly incident on the second glass substrate 416. Heat mirror 418 may be disposed below the first acrylic layer 408 so as to reflect at least some of the radiation (e.g., UV and IR radiation) transmitted through the second glass substrate 416, second gas layer 414, fluid channel layer 410 and acrylic layers 408, 412. As is known in the art, heat mirror film is a transparent film which contains nano-scale coatings of metal that reflect heat back to its source. Each gas layer 406, 414 may have a thickness within a range of 0.5 to 0.75 inches, for example. The fluid channel layer 410 may be formed by channels and/or wells formed directly in one or both of the acrylic layers 408, 412, or by channels and/or wells formed in a separate glass layer formed between the acrylic layers. The surfaces of the acrylic layers 408, 412 disposed closest to the fluid channel layer 410 may be coated with silicon carbide to increase heating.

Uses contemplated for various embodiments included but are not limited to small to large format, substantially transparent, power generating windows and covers, and smart window technology for ambient optical conditioning and visual enhancement. Programmability and erasability of the panels are contemplated including the ability to display transmitted visual images by retaining fluid properties within well like structures and to record disruptions to the thermal or flow properties of fluids within channels resulting from pressure or input radiation fields.

As mentioned, the microfluidic panel may also be adapted for optical processing. In this regard, diffraction effects may be achieved through index changes in fluid grating within the microfluidic panel. The particular fluid selected for such an application may exhibit thermoptic properties, so that application of heat at specific locations within the panel may result in the desired grating effect caused by localized thermal transfer to the fluid within the channels. Suitable fluids having such thermoptic properties include, for example, water (possibly with dye added for color and absorption properties), salt water, liquid crystal materials as used in displays, hydrogen peroxide, and sulfuric acid, to name a few.

According to another exemplary embodiment of the microfluidic panel adapted for optical processing, dyes may be introduced to the channel fluid using, for example, microvalves. The dye may be used to generate darkening effects by introducing the dye into fluid in the channels that is otherwise substantially optically transparent. The microvalves may be controlled locally to generate grating effects at a rapid rate to achieve specific applications in, for example, transparent smart window technology or touchscreen display devices.

Now that embodiments of the present invention have been shown and described in detail, various modifications and improvements thereon will become readily apparent to those skilled in the art. Accordingly, the spirit and scope of the present invention is to be construed broadly and not limited by the foregoing specification.

What is claimed is:

1. A microfluidic panel comprising:
   at least one substrate;
   one or more channels formed in the substrate; and
   a fluid disposed within the one or more channels, wherein the fluid is selected to store thermal energy and the microfluidic panel is adapted to convert the thermal energy into useable energy.

2. The microfluidic panel of claim 1, further comprising a cover disposed over the substrate.

3. The microfluidic panel of claim 1, wherein the at least one substrate is made of glass.

4. The microfluidic panel of claim 3, wherein the glass comprises one or more types of glass selected from the group consisting of: fused silica glass, borosilicate glass and photostructurable glass.

5. The microfluidic panel of claim 1, wherein the one or more channels comprise a plurality of channels that form a grid.

6. The microfluidic panel of claim 1, wherein the one or more channels comprise a channel that follows a serpentine path.

7. The microfluidic panel of claim 1, further comprising at least one thermoelectric generator.

8. The microfluidic panel of claim 1, further comprising at least one pump that causes the fluid to flow through the one or more channels.

9. The microfluidic panel of claim 8, wherein the at least one pump is a micro-electromechanical system (MEMS) pump.

10. The microfluidic panel of claim 1, wherein the at least one substrate comprises:
    a first glass layer;
    a first gas layer formed over the first glass layer;
    a first acrylic layer formed over the first gas layer;
    a second acrylic layer formed over the first acrylic layer;
    a second gas layer formed over the second acrylic layer; and
    a second glass layer formed over the second gas layer.

11. The microfluidic panel of claim 10, wherein the one or more channels are formed in at least one of the first or second acrylic layers.

12. The microfluidic panel of claim 10, wherein the one or more channels are formed in a glass substrate disposed between the first and second acrylic layers.

13. The microfluidic panel of claim 10, further comprising heat mirror disposed below the first acrylic layer.

14. The microfluidic panel of claim 10, wherein surfaces of the first and second acrylic layers closest to the one or more channels are coated with silicon carbide.

15. A microfluidic panel comprising:
    at least one substrate;
    one or more channels formed in the substrate; and
    a fluid disposed within the one or more channels, wherein the fluid is selected to store thermal energy and the microfluidic panel is adapted to condition the energy to adjust optical wavelength passband of the panel.

16. A microfluidic panel comprising:
    at least one substrate;
    one or more channels formed in the substrate; and
    a fluid disposed within the one or more channels, wherein the at least one substrate comprises:
    a first glass layer;
    a first gas layer formed over the first glass layer;
    a first acrylic layer formed over the first gas layer;
    a second acrylic layer formed over the first acrylic layer;
    a second gas layer formed over the second acrylic layer; and
    a second glass layer formed over the second gas layer.

17. The microfluidic panel of claim 16, wherein the one or more channels are formed in at least one of the first or second acrylic layers.

18. The microfluidic panel of claim 16, wherein the one or more channels are formed in a glass substrate disposed between the first and second acrylic layers.

* * * * *